US011833280B2

(12) United States Patent
Amra et al.

(10) Patent No.: US 11,833,280 B2
(45) Date of Patent: Dec. 5, 2023

(54) APPARATUS CONFIGURED TO BE USED WITH A BREAST PUMP DEVICE

(71) Applicant: KONINKLIJKE PHILIPS N.V., Eindhoven (NL)

(72) Inventors: Eyob Atnafu Amra, Eindhoven (NL); Daan Hendrik Gosenshuis, Waarle (NL); Robert Frans Maria Hendriks, Overlangel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 748 days.

(21) Appl. No.: 16/629,443

(22) PCT Filed: Jul. 3, 2018

(86) PCT No.: PCT/EP2018/067864
§ 371 (c)(1),
(2) Date: Jan. 8, 2020

(87) PCT Pub. No.: WO2019/011707
PCT Pub. Date: Jan. 17, 2019

(65) Prior Publication Data
US 2021/0128805 A1 May 6, 2021

(30) Foreign Application Priority Data
Jul. 10, 2017 (EP) ..................................... 17180433

(51) Int. Cl.
*A61M 1/06* (2006.01)
(52) U.S. Cl.
CPC .............. *A61M 1/06* (2013.01); *A61M 1/062* (2014.02); *A61M 1/0697* (2021.05);
(Continued)

(58) Field of Classification Search
CPC ................................. A61M 1/06; A61M 1/062
See application file for complete search history.

(56) References Cited

U.S. PATENT DOCUMENTS

2005/0099314 A1* 5/2005 Aisa .................... H02J 13/0001
340/637
2009/0192927 A1* 7/2009 Berg .................... H01R 13/717
705/412

(Continued)

FOREIGN PATENT DOCUMENTS

AU 781102 B2 5/2005
EP 2833937 2/2015

(Continued)

OTHER PUBLICATIONS

International Search Report and Written Opinion dated Oct. 15, 2018 For International Application No. PCT/EP2018/067864 Filed Jul. 3, 2018.

*Primary Examiner* — William R Carpenter

(57) ABSTRACT

The invention relates to an apparatus (10) for collecting information related to operation of a breast pump device (1) comprising a pump (31) and a circuit (32) for supplying electric power to the pump (31). The apparatus (10) is accommodated in a power adapter of the device (1) and comprises a detection unit (11) that is configured to detect an electric signal on the circuit (32) of the device (1), a processing unit (12) that is configured to receive the detected electric signal from the detection unit (11) and to process the detected electric signal according to a preset routine in order to generate an information signal representative of information related to use of the device (1), and a transmission unit (13) that is configured to receive the information signal from the processing unit (12) and to transmit the information signal to an external device such as a smartphone (6).

20 Claims, 2 Drawing Sheets

(52) U.S. Cl.
CPC . *A61M 1/06935* (2021.05); *A61M 2205/3317* (2013.01); *A61M 2205/3561* (2013.01); *A61M 2205/3576* (2013.01); *A61M 2205/50* (2013.01)

(56) References Cited

U.S. PATENT DOCUMENTS

| | | | |
|---|---|---|---|
| 2010/0280978 A1* | 11/2010 | Shimada | H02J 13/00028 |
| | | | 706/54 |
| 2012/0013442 A1 | 1/2012 | Lee | |
| 2013/0073257 A1* | 3/2013 | Williams | G01R 31/3274 |
| | | | 702/179 |
| 2013/0317837 A1 | 11/2013 | Ballantyne | |
| 2014/0236079 A1* | 8/2014 | Sella | A61M 1/06 |
| | | | 604/74 |
| 2015/0366530 A1 | 12/2015 | Ku | |
| 2016/0000982 A1 | 1/2016 | Alvarez | |
| 2016/0082166 A1 | 3/2016 | Guthrie | |
| 2016/0287767 A1 | 10/2016 | Simmons | |
| 2016/0296682 A1 | 10/2016 | Phillips | |
| 2016/0303298 A1 | 10/2016 | Makower | |

FOREIGN PATENT DOCUMENTS

| | | | |
|---|---|---|---|
| WO | WO-0001431 A1 * | 1/2000 | A61M 1/062 |
| WO | WO-2014044423 A1 * | 3/2014 | A61M 1/06 |
| WO | WO-2014044472 A1 * | 3/2014 | A61M 1/0031 |
| WO | 2014/058430 | 4/2014 | |
| WO | 2016/025405 | 2/2016 | |
| WO | 2016/162757 | 10/2016 | |

* cited by examiner

APPARATUS CONFIGURED TO BE USED WITH A BREAST PUMP DEVICE

CROSS REFERENCE TO RELATED APPLICATIONS

This application is the U.S. National Phase application under 35 U.S.C. § 371 of International Application No. PCT/EP2018/067864 filed Jul. 3, 2018, published as WO 2019/011707 on Jan. 17, 2019, which claims the benefit of European Patent Application Number 17180433.9 filed Jul. 10, 2017. These applications are hereby incorporated by reference herein.

FIELD OF THE INVENTION

The invention relates to an apparatus, configured to be used with a breast pump device for the purpose of collecting information related to operation of a breast pump device, particularly an electric breast pump device comprising an expression kit for subjecting a breast to a pressure profile and receiving milk expressed from the breast, a pump for creating the pressure profile in the expression kit, and an electric power supply circuit for supplying power to the pump, the apparatus comprising: a detection unit that is configured to detect an electric signal on the electric power supply circuit of the breast pump device, a processing unit that is configured to receive the detected electric signal from the detection unit and to process the detected electric signal according to a preset routine in order to generate an information signal representative of information related to use of the breast pump device, and a transmission unit that is configured to receive the information signal from the processing unit and to transmit the information signal for enabling receipt of the information signal by an external device.

The invention also relates to a breast pump device, particularly an electric breast pump device comprising an expression kit for subjecting a breast to a pressure profile and receiving milk expressed from the breast, a pump for creating the pressure profile in the expression kit, an electric power supply circuit for supplying power to the pump, and a power adapter.

The invention further relates to a power adapter of a breast pump device, particularly an electric breast pump device comprising an expression kit for subjecting a breast to a pressure profile and receiving milk expressed from the breast, a pump for creating the pressure profile in the expression kit, and an electric power supply circuit for supplying power to the pump.

BACKGROUND OF THE INVENTION

In general, breast pump devices are well known devices for extracting milk from a breast of a user, or two breasts simultaneously. A breast pump device may be used in various situations, for example, if a baby or infant is not able to extract milk from the breast, or if a mother is separated from her baby or infant and the baby or infant is to be fed with breast milk at a later stage, by the mother or another person. In other words, breast pump devices are used by women to express breast milk at a convenient time, to be stored for later consumption by their/a child. A breast pump device may also be helpful in a situation in which it is desired to stimulate and increase milk production in women with a low milk supply.

A breast pump device is typically operated with one or two expression kits. Among other things, an expression kit comprises a breast-receiving funnel for receiving a user's breast, which funnel may be equipped with pads or the like for massaging the breast in a certain way, and is designed for connection to a vacuum unit for realizing a pressure cycle in the breast-receiving funnel, by means of which milk expression from the breast is enabled. In practical cases, the vacuum unit comprises an electric vacuum pump. The fact is that by generating a pressure cycle, particularly a vacuum cycle, possibly accompanied by a certain way of massaging the breast, a simulation of a feeding action is obtained, which triggers the necessary let-down reflex in the user of the breast pump device.

In the field of breast pump devices, there is a need for ways to keep track of information related to use of a breast pump device. For example, it may be desirable to know how many pumping sessions have been performed by means of a breast pump device in a certain time period, how long the respective pumping sessions lasted, which modes of operation were chosen in the respective pumping sessions, etc.

WO 2014/058430 A1 relates to a breast pump device that comprises a pump for generating suction and a controller configured to control the pump to generate different suction levels in a cyclic manner at a frequency, to control the pump to start and stop pumping, to collect input from a user of an amount of milk collected, and to store information for at least one pumping session. In an embodiment, the breast pump device comprises a graphical user interface on a touch screen display for the controller. The graphical user interface includes a pump control tab having one or more of a start/stop button, a session duration time clock, a suction control portion, and a speed control portion, a milk volume entry tab having one or more of a left milk volume entry portion, a right milk volume entry portion, a save button, and a session information portion; and a session history tab having one or more of scrolling control portions, and a session history information portion. The tabs provide a way for a user to switch between various modes of operation, e.g. pump control, milk volume entry, and viewing of session history. The touch screen display may display at least one of session duration time, current pump suction level, current cycle speed level, current volume status (e.g. on or mute), and current battery status. In addition, the touch screen display may provide session history information for one or more pumping sessions that have been saved by the user, including one or more of: date, time, left milk volume level, right milk volume level, suction level, speed, and duration.

US 2016/287767 A1 relates to a breast pump system that may communicate with various electronic devices and/or server components to exchange data and perform certain functionalities. The functionalities may include providing visual and audio feedback to a user, supporting unique kit identification as well as associated user profiles and preferred configuration settings, enabling effective labeling of collection containers, and determining volume and flow of expressed breast milk. In a practical embodiment, the system includes an electronic device that can be selectively connected to the breast pump system and a processing server that can be selectively connected to either or both of the breast pump system and the electronic device. The electronic device may include a user interface configured to display certain information and receive selections and inputs from the user. During operation, a pressure level may be determined by detecting a measure of at least one of a force in a volume displacement component of the system, a temperature drop, and a motor armature current.

SUMMARY OF THE INVENTION

It is an object of the invention to provide a way of collecting information related to operation of a breast pump that does not involve a need to change the design of existing breast pump devices that are without information functionality. Further, the invention is aimed at obtaining a very high level of accuracy and reliability of the information collecting process.

According to the invention, an apparatus is provided that is configured to be used with a breast pump device for the purpose of collecting information related to operation of a breast pump device, particularly an electric breast pump device comprising an expression kit for subjecting a breast to a pressure profile and receiving milk expressed from the breast, a pump for creating the pressure profile in the expression kit, and an electric power supply circuit for supplying power to the pump, which apparatus comprises: a detection unit that is configured to detect an electric signal on the electric power supply circuit of the breast pump device, a processing unit that is configured to receive the detected electric signal from the detection unit and to process the detected electric signal according to a preset routine in order to generate an information signal representative of information related to use of the breast pump device, and a transmission unit that is configured to receive the information signal from the processing unit and to transmit the information signal for enabling receipt of the information signal by an external device, wherein the apparatus is accommodated in a power adapter of the breast pump device.

The invention relies on detecting an electric signal on the electric power supply circuit of a breast pump device, which appears to involve the advantage that the apparatus according to the invention can be provided as an add-on in the design of a breast pump device. In other words, the apparatus according to the invention can come as a separate component that is coupled to a breast pump device in such a way as to be able to detect the electric signal as mentioned. In any case, for the purpose of realizing the invention, there is no need for having any physical sensor in the pumping parts of a breast pump device. An insight underlying the invention is that the electric signal can be very well be used as an indicator of operational aspects of a breast pump device, particularly operational aspects of the pump thereof.

In comparison to collecting information from settings in a controller of a breast pump device, detecting an electric signal on the electric power supply circuit of a breast pump device yields better results in terms of accuracy and reliability. When the invention is put to practice, actual values are measured, whereas in the conventional situation, any deviations between settings and actual values affect accuracy and reliability of the information that is eventually provided to a user, which may cause the user to draw incorrect conclusions or to miss certain defects that may occur.

In respect of the physical location of the apparatus according to the invention with respect to a breast pump device, it is to be noted that the apparatus is accommodated in a power adapter of the breast pump device. This allows for adding the apparatus in its entirety to the breast pump device during manufacturing.

According to a practical possibility existing within the framework of the invention, the detection unit may be configured to detect the system current on the electric power supply circuit of a breast pump device by performing current measurements. For example, the detection unit may be configured to perform a shunt measurement, and may optionally comprise a plug-in current transformer, or the detection unit may be equipped with a Hall effect sensor. Assuming that the current drawn by the pump during operation thereof is at a fixed voltage, which is normally the case in consumer electronics connected to the mains or using a battery, the current is a suitable indicator of the power consumption of the pump.

Basically, the processing unit may be configured to determine an operational status of the pump of the breast pump device to be an inactivated status when a value of the detected electric signal is zero and to be an activated status on the basis of a value higher than zero of the detected electric signal, and to generate an information signal representative of the operational status of the pump through time. In such a case, the apparatus according to the invention is suitable to be used for determining whether the pump is on or off, thereby providing a diary to the user of the breast pump device.

According to a further option, the processing unit may be configured to determine a power level of operation of the pump of the breast pump device on the basis of a value of the detected electric signal, and to generate an information signal representative of the power level of operation of the pump through time. In such a case, the apparatus according to the invention is suitable to be used for detecting the power consumed by the breast pump device, from which the setting and actual use of the pump could be derived. As mentioned earlier, detecting power can be done by performing current measurements assuming that a power source of the breast pump device provides a fixed voltage.

According to yet a further option, the processing unit may be configured to determine a mode of operation of the pump of the breast pump device to be one of a number of preset modes of operation by comparing a value profile of the detected electric signal through time to value profiles of the electric signal associated with the respective modes of operation, and to generate an information signal representative of the mode of operation of the pump through time. In such a case, the apparatus according to the invention is suitable to be used for analyzing variation of power consumption (represented by current drawn) over time, thereby deriving, for example, periodicity and shape of a repeating pattern. This even further enables a detection of settings and use, allowing specifically to detect the load of the pump, which offers a possibility of providing a user with guidance on how to correct usage.

It is advantageous for the detection unit to be configured to detect the electric signal through a power-line communication protocol. This is a form of digital communication that is well known and that could be applied as a standardized or proprietary protocol in the context of the invention. In any case, through a power-line communication protocol, other sensorial data could be added to the collected power-related information, such as data on use like milk volume, data related to maintenance, and data related to overall use rather than instantaneous use.

In a practical embodiment of the apparatus according to the invention, the transmission unit is configured to transmit the information signal through wireless data transmission. For example, Bluetooth or Wi-Fi may be used for conveying data to e.g. a mobile app or a connected device. In general, the external device for receiving the information signal from the apparatus may be a user-readable device of any suitable type.

Further, the invention relates to a breast pump device, particularly an electric breast pump device comprising an expression kit for subjecting a breast to a pressure profile and receiving milk expressed from the breast, a pump for creating the pressure profile in the expression kit, an electric power supply circuit for supplying power to the pump, and a power adapter accommodating an apparatus as described in the foregoing.

Still further, the invention relates to a power adapter of a breast pump device, particularly an electric breast pump device comprising an expression kit for subjecting a breast to a pressure profile and receiving milk expressed from the breast, a pump for creating the pressure profile in the expression kit, and an electric power supply circuit for supplying power to the pump, the power adapter accommodating an apparatus as described in the foregoing.

The above-described and other aspects of the invention will be apparent from and elucidated with reference to the following detailed description of various possibilities relating to the concept of detecting an electric signal on the electric power supply circuit for supplying power to the pump of a breast pump device, and generating an information signal representative of information related to use of the breast pump device by processing the detected electric signal.

BRIEF DESCRIPTION OF THE DRAWINGS

The invention will now be explained in greater detail with reference to the figures, in which equal or similar parts are indicated by the same reference signs, and in which.

DETAILED DESCRIPTION OF EMBODIMENTS

Figure 1:
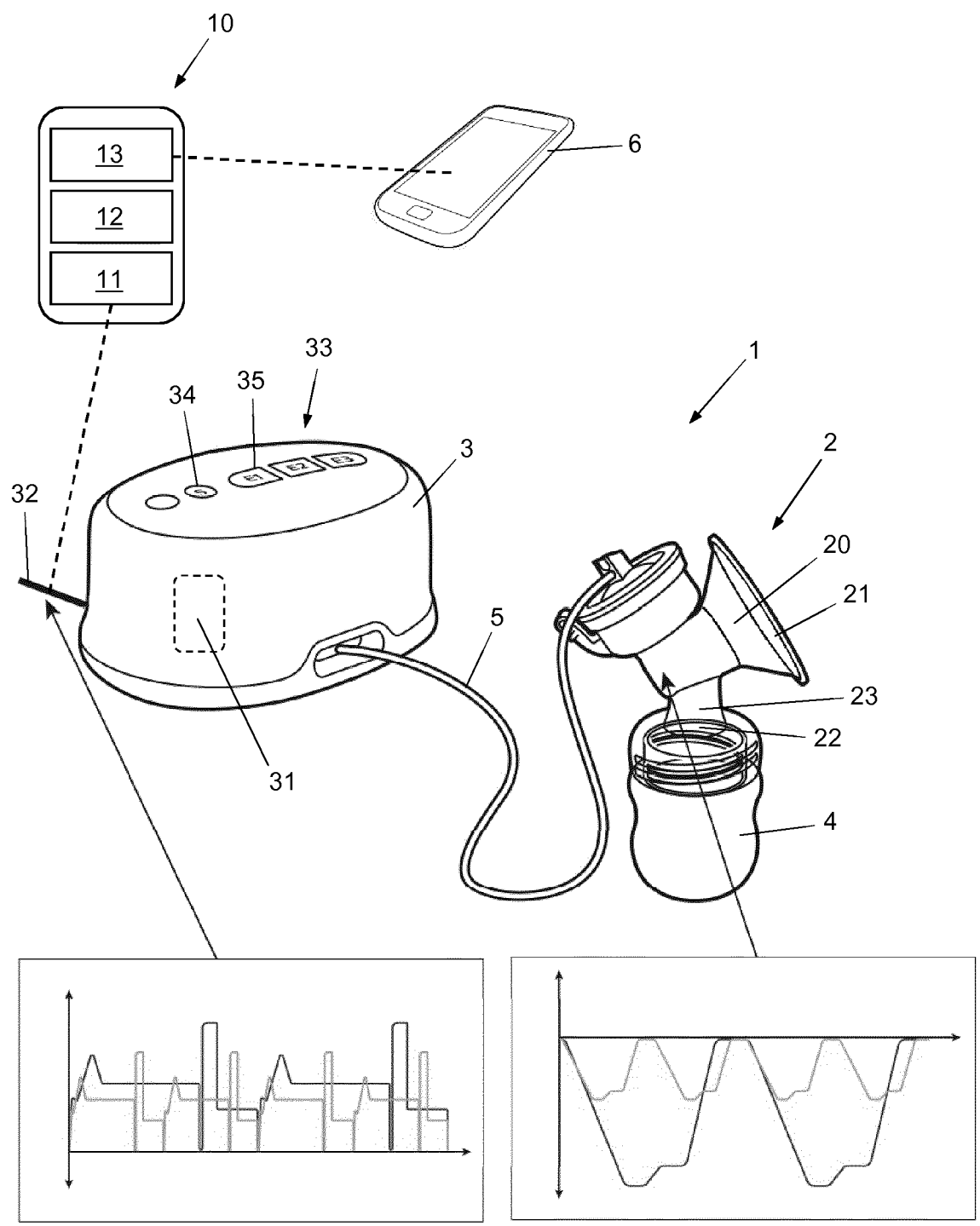
FIG. 1 diagrammatically shows a breast pump device comprising a vacuum unit, an expression kit, and a flexible hose interconnecting the vacuum unit and the expression kit, also diagrammatically shows an apparatus according to the invention, for collecting information related to operation of a breast pump device, and a user-readable device for receiving information from the apparatus, and further diagrammatically shows a graph representing a detected profile of the system current and a graph representing a profile of the pumping pressure as determined on the basis of the detected profile of the system current by applying the invention.

The invention is in the field of breast pump devices, particularly electric breast pump devices. With reference to FIG. 1, a general description of an electric breast pump device will be given so as to generate a clear picture of the context in which the invention is applicable.

The breast pump device 1 comprises an expression kit 2 and a vacuum unit 3 for generating a pressure cycle during which vacuum is alternately created and released. The expression kit 2 comprises a functional expression body 20 and a milk receptacle 4 that is connectable to the expression body 20, e.g. by screwing, thereby closing a lower end of the expression body 20. The vacuum unit 3 is an electric vacuum unit and comprises an electric pump 31 and an air valve for realizing an alternating vacuum during operation, i.e. during pumping sessions to be performed by means of the breast pump device 1. The pump 31 is only diagrammatically depicted in FIG. 1 as a dashed rectangle, whereas the air valve and other components of the vacuum unit 3 as will be mentioned in the following are not shown. The pump 31, the air valve and associated controller for realizing proper operation of the pump 31 and the air valve are designed to function in a manner that is well known in the field of breast pump devices. Therefore, further details of these components will not be further explained in the present text, and the same is applicable to other practical aspects of the vacuum unit 3 known per se. The pump 31 is electrically connected to a source of electric power, which may be the mains or a battery, for example. In FIG. 1, a line 32 projecting from the vacuum unit 3 is shown that is to be regarded as being representative of an electric circuit for supplying power to the pump 31, which does not alter the fact that such a line 32 may be located in the vacuum unit 3 only, which may be the case when the power source is located in the vacuum unit 3 and/or arranged directly on/against the vacuum unit 3, for example. In any case, the word "line" in this respect should not be understood such as to be limited to a physical line, as it is used for the purpose of including any way in which power supply to the pump 31 may be realized and to represent any possible embodiment of an electric power supply circuit.

The expression body 20 comprises a breast-receiving funnel 21, an aperture acting as a milk outlet 22, and a milk path 23 from the breast-receiving funnel 21 to the milk outlet 22. The breast-receiving funnel 21 is thus in fluid communication with the milk outlet 22 through the milk path 23. The breast-receiving funnel 21 can comprise a massage cushion or the like (not shown) for providing a soft and warm feel to the breast and/or imitating a baby's sucking action.

In FIG. 1, the breast pump device 1 is shown in an assembled condition, in which the vacuum unit 3 is connected to the expression kit 2 through a flexible hose 5. Such a configuration allows for a remote arrangement of the vacuum unit 3 with respect to the expression kit 2, so that the size of that part of the breast pump device 1 that is to be applied to a user's breast can be kept within reasonable limits. It is to be noted that the breast pump device 1 can comprise two expression kits 2 for enabling a user of the breast pump device 1 to extract milk from two breasts at the same time, in which case the expression kits 2 can share a common vacuum unit 3.

Advantageously, as shown, the breast pump device 1 comprises a user interface 33 for allowing a user to control operation of the breast pump device 1. In the shown example, the user interface 33 is arranged on the vacuum unit 3 and enables a user to provide input to the controller of the vacuum unit 3. The user interface 33 may be realized in any suitable manner such as through a number of buttons 34, 35 as shown, or through a touch screen, for example. By way of example, it is noted that the user interface 33 may comprise one button 34 for activating a stimulation mode and three buttons 35 for choosing one of three expression settings.

The invention provides a way of automatically saving and tracking aspects of pumping sessions, such as expression setting, expression time, most used setting, etc. On the basis thereof, a user of the breast pump device 1 is enabled to follow a milk expression session and/or to log the history, wherein user-readable devices such as smartphones, tablets or laptops may be used for displaying the information to the user. For the sake of completeness, it is noted that the user to be provided with information does not necessarily need to be the same person as the woman who actually uses the breast pump device 1, as the information may also be relevant to a nurse or a physician, for example.

In FIG. 1, an apparatus 10 according to the invention, which serves for collecting information related to operation of the breast pump device 1, is diagrammatically shown. In the following, for the sake of clarity, the apparatus 10 will be referred to as information tracker 10.

In the first place, it is noted that the information tracker 10 is arranged to perform measurements on the electric power supply circuit 32 of the breast pump device 1, as diagrammatically indicated in FIG. 1 by means of a dashed line. Further, a notable fact is that the information tracker 10 comprises three units 11, 12, 13, which are different units 11, 12, 13 as far as their functionality is concerned, but which do not necessarily need to be physically separated units. A first unit is a detection unit 11 that is configured to detect an electric signal on the electric power supply circuit 32 of the breast pump device 1. In the following, it is assumed that the detection unit 11 is especially adapted to perform current measurements and to thereby detect the system current. A second unit is a processing unit 12 that is configured to receive the detected electric signal from the detection unit 11 and to process the detected electric signal according to a preset routine in order to generate an information signal representative of information related to use of the breast pump device 1. Analyzing detected system current is a practical way of obtaining the information as desired, as will be explained later. A third unit is a transmission unit 13 that is configured to receive the information signal from the processing unit 12 and to transmit the information signal for enabling receipt of the information signal by an external device such as a smartphone 6. Communication between the transmission unit 13 and the external device is preferably realized in a wireless fashion, as diagrammatically indicated in FIG. 1 by means of a dashed line.

The detection unit 11 may be designed in any suitable way for performing current measurements. In general, an advantage of performing current measurements is that this can be done by means of a unit that is arranged as an additional component to an existing device. This means that the basic set-up of the device does not need to be changed when it is desired to introduce a current measuring functionality.

In general, an electric current is a flow of electric charge. Electric circuits may comprise wiring, in which case the charge is carried by electrons moving through the wiring. The SI unit for measuring an electric current is ampere, which is the flow of electric charge across a surface at the rate of one coulomb per second. Different possibilities exist for measuring electric current in consumer electronics. According to a first practical possibility, current measurement is performed using a low-ohm resistor, also known as shunt, and which is suitable for connection in parallel to a voltmeter and connection in series with a load of which the system current is to be measured. The system current is proportional to the current measured at the shunt, which follows from the general equation I=V/R. The shunt can be located upstream or downstream of the load. In addition, a plug-in current transformer may be used, which is designed to function according to the transformer principle and to expand the range of an existing measurement system, usually a shunt transformer. The number of secondary windings of a plug-in current transformer mirrors a fixed setting of the division ratio of the transformer. According to a second practical possibility, a Hall effect sensor is used, in which case a soft-magnetic, ring-shaped core is applied around a conductor, and the sensor is located in a small air gap that is present in the core. A magnetic flux is generated in the core by the current flowing through the conductor. The magnetic flux also flows through the sensor, which outputs a voltage signal proportional to the detected current as a result.

The processing unit 12 may comprise a microprocessor and can be programmed with any suitable algorithms, preset data etc. Following an algorithm for processing data may include using at least one look-up table. Depending on the specifics of the processing unit 12, it is possible to keep track of the settings that are directly related to milk expression, as mentioned, and it is also possible to measure other aspects such as whether a situation can be classified as loaded or unloaded, the amount of load, which can be used as an indication of nipple size, and change of power consumption over time, which can be used as an indication of wear.

The information collection from the breast pump device 1 can be executed in different forms, as will now be explained. In a most basic case, the information tracker 10 is configured to measure whether the pump 31 is on or off, thereby providing a diary to the user. In a more advanced form, the information tracker 10 is configured to measure the power consumed by the breast pump device 1, from which the setting and actual use of the pump 31 can be derived. Measuring power is done through measuring the system current assuming that the power source provides a fixed voltage. According to a further possibility, the information tracker 10 is configured to analyze variation of power consumption over time, thereby deriving, for example, periodicity and shape of a repeating pattern. This even further enables the detection of settings and use. Specifically, this allows to detect the load of the pump 31, which offers a possibility of providing a user with guidance on how to correct usage. In a most advanced form, digital communication between the information tracker 10 and the pump 31 is done through a power-line communication protocol, which may be standardized or proprietary. Through such a protocol, the collected information may be enriched by adding other sensorial data collected at the pump 31.

In FIG. 1, for the purpose of providing an illustration of the analysis that is done in the information tracker 10, a graph of results of two different current measurements is shown at the left side of the figure. The x axis of the graph represents time, whereas the y axis of the graph represents the value of the current. It is clear that one of the graphs is characterized by relatively low values with respect to the x axis and relatively short time intervals, whereas the other of the graphs is characterized by relatively high values with respect to the x axis and relatively long time intervals. In the processing unit 12, the results of the current measurements are processed in order to find the associated pressure profile. A graph of two pressure profiles that are derived from the results of the two different current measurements is shown at the right side of FIG. 1. The x axis of the graph represents time, whereas the y axis of the graph represents the value of the pressure. Again, one of the graphs is characterized by relatively low values with respect to the x axis and relatively short time intervals, and the other of the graphs is characterized by relatively high values with respect to the x axis and relatively long time intervals, being directly related to the corresponding graphs of the results of the current measurements. In FIG. 1, the locations to which the respective graphs are applicable are diagrammatically indicated by means of arrows extending between the respective graphs and the locations.

By determining a pressure profile on the basis of a detected system current profile, it is possible to identify in which setting the pump 31 was used and how long the pumping session lasted. These data are examples of information as may be transmitted to the external device. Identifying the setting of the pump 31 may be done by assessing the periodicity of the measurement results, assuming that each of the settings has a typical timing.

Figure 2:
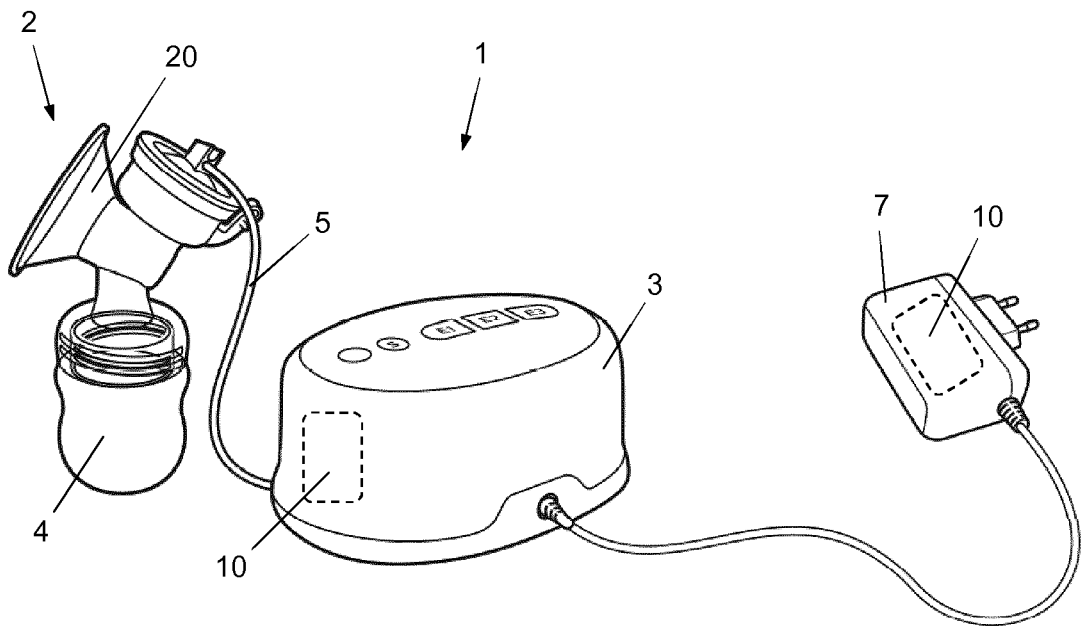
FIG. 2 diagrammatically shows the breast pump device with a power adapter.

In principle, the information tracker 10 can be arranged at any suitable position with respect to the breast pump device 1. With reference to FIG. 2, it is noted that the information tracker 10 may be located in the vacuum unit 3, as diagrammatically indicated in FIG. 2 by means of a dashed rectangle at the position of the vacuum unit 3. Another possible location is a location according to the invention, namely a location in a power adapter 7 of the breast pump device 1, as diagrammatically indicated in FIG. 2 by means of a dashed rectangle at the position of a power adapter 7.

Figure 3:
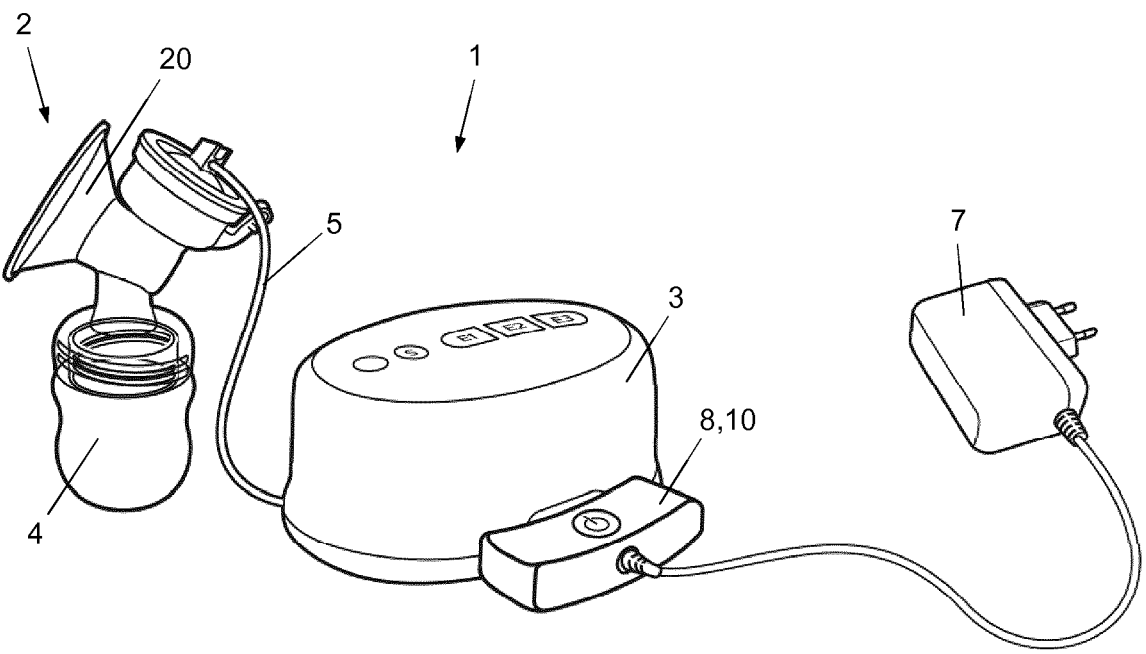
FIG. 3 diagrammatically shows the breast pump device with a power adapter and a dongle.

Another option is illustrated in FIG. 3, namely the option of the information tracker 10 being provided in the form of a dongle 8. In the shown example, a dongle 8 is adapted to be connected between the vacuum unit 3 and the power adapter 7. In any case, according to the invention, the information tracker 10 can be regarded as a functional apparatus that is added in its entirety to the breast pump device 1, in one of the components of the breast pump device 1 during manufacturing, namely the power adapter 7.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

The invention claimed is:

1. An apparatus and a power adapter of a breast pump device, wherein the apparatus is configured to be used with the breast pump device for the purpose of collecting information related to operation of the breast pump device, the breast pump device comprising an expression kit, a pump, and an electric power supply circuit for supplying power to the pump, and the apparatus comprising:
   a detection unit that is configured to detect an electric signal on the electric power supply circuit of the breast pump device,
   a processing unit that is configured to receive the detected electric signal from the detection unit and to process the detected electric signal according to a preset routine in order to generate an information signal representative of information related to use of the breast pump device, and
   a transmission unit that is configured to receive the information signal from the processing unit and to transmit the information signal for enabling receipt of the information signal by an external device,
   wherein the apparatus is accommodated in the power adapter of the breast pump device, wherein the processing unit of the apparatus is configured to correlate a breast pump mode of operation of the pump of the breast pump device with the detected electric signal by determining and identifying the breast pump mode of operation to be one of a number of preset breast pump modes of operation, and to generate an information signal representative of the breast pump mode of operation of the pump through time.

2. The apparatus and the power adapter according to claim 1, wherein the detection unit of the apparatus is configured to detect a system current on the electric power supply circuit of the breast pump device by performing current measurements.

3. The apparatus and the power adapter according to claim 2, wherein the detection unit of the apparatus is configured to perform a shunt measurement.

4. The apparatus and the power adapter according to claim 3, wherein the detection unit of the apparatus comprises a plug-in current transformer.

5. The apparatus according to claim 2, wherein the detection unit of the apparatus comprises a Hall effect sensor.

6. The apparatus and the power adapter according to claim 1, wherein the processing unit of the apparatus is configured to determine an operational status of the pump of the breast pump device to be an inactivated status when a value of the detected electric signal is zero and to be an activated status on the basis of a value higher than zero of the detected electric signal, and to generate an information signal representative of the operational status of the pump through time.

7. The apparatus and the power adapter according to claim 1, wherein the processing unit of the apparatus is configured to determine a power level of operation of the pump of the breast pump device on the basis of a value of the detected electric signal, and to generate an information signal representative of the power level of operation of the pump through time.

8. The apparatus and the power adapter according to claim 1, wherein the processing unit of the apparatus is configured to correlate the breast pump mode of operation of the pump of the breast pump device with the detected electric signal by determining and identifying the breast pump mode of operation to be one of the number of preset breast pump modes of operation by comparing a value profile of the detected electric signal through time to value profiles of the electric signal correlated with the respective breast pump modes of operation.

9. The apparatus and the power adapter according to claim 1, wherein the detection unit of the apparatus is configured to detect the electric signal through a power-line communication protocol.

10. The apparatus and the power adapter according to claim 1, wherein the transmission unit of the apparatus is configured to transmit the information signal through wireless data transmission.

11. A method of operating an apparatus and a power adapter of a breast pump device, wherein the apparatus is configured to be used with the breast pump device for the purpose of collecting information related to operation of the breast pump device, the breast pump device comprising an expression kit, a pump, and an electric power supply circuit for supplying power to the pump, and the method comprising:
  detecting, by a detection unit of the apparatus, an electric signal on the electric power supply circuit of the breast pump device,
  receiving, by a processing unit of the apparatus, the detected electric signal from the detection unit;
  processing, by the processing unit of the apparatus, the detected electric signal according to a preset routine, by correlating a breast pump mode of operation of the pump of the breast pump device with the detected electric signal by determining and identifying the breast pump mode of operation to be one of a number of preset breast pump modes of operation;
  generating an information signal representative of the breast pump mode of operation of the pump through time;
  receiving, by a transmission unit of the apparatus, the information signal from the processing unit; and
  transmitting, by the transmission unit of the apparatus, the information signal for enabling receipt of the information signal by an external device,
  wherein the apparatus is accommodated in the power adapter of the breast pump device.

12. The method of operating the apparatus and the power adapter according to claim 11, further comprising:
  detecting, by the detection unit of the apparatus, a system current on the electric power supply circuit of the breast pump device by performing current measurements.

13. The method of operating the apparatus and the power adapter according to claim 12, further comprising:
  performing, by the detection unit of the apparatus, a shunt measurement.

14. The method of operating the apparatus and the power adapter according to claim 13,
  wherein the detection unit of the apparatus comprises a plug-in current transformer.

15. The method of operating the apparatus and the power adapter according to claim 12,
  wherein the detection unit of the apparatus comprises a Hall effect sensor.

16. The method of operating the apparatus and the power adapter according to claim 11,
  determining, by the processing unit of the apparatus, an operational status of the pump of the breast pump device to be an inactivated status when a value of the detected electric signal is zero and to be an activated status on the basis of a value higher than zero of the detected electric signal, and
  generating, by the processing unit of the apparatus, an information signal representative of the operational status of the pump through time.

17. The method of operating the apparatus and the power adapter according to claim 11,
  determining, by the processing unit of the apparatus, a power level of operation of the pump of the breast pump device on the basis of a value of the detected electric signal, and
  generating, by the processing unit of the apparatus, an information signal representative of the power level of operation of the pump through time.

18. The method of operating the apparatus and the power adapter according to claim 11, further comprising:
  correlating, by the processing unit of the apparatus, the breast pump mode of operation of the pump of the breast pump device with the detected electric signal by determining and identifying the breast pump mode of operation to be one of the number of preset breast pump modes of operation by comparing a value profile of the detected electric signal through time to value profiles of the electric signal correlated with the respective breast pump modes of operation.

19. The method of operating the apparatus and the power adapter according to claim 11,
  detecting, by the detection unit of the apparatus, the electric signal through a power-line communication protocol.

20. The method of operating the apparatus and the power adapter according to claim 11,
  transmitting, by the transmission unit of the apparatus, the information signal through wireless data transmission.

* * * * *